United States Patent [19]

Renga et al.

[11] Patent Number: 4,927,508

[45] Date of Patent: May 22, 1990

[54] ALKYL 2-FLUORO-1-METHOXYETHYLCARBAMATES

[75] Inventors: James M. Renga, Walnut Creek; Charles K. Pon, Concord; Aylin H. Gulbenkian; Michael G. Smith, both of Walnut Creek, all of Calif.

[73] Assignee: The Dow Chemical Company, Midland, Mich.

[21] Appl. No.: 307,397

[22] Filed: Feb. 7, 1989

Related U.S. Application Data

[62] Division of Ser. No. 154,762, Feb. 11, 1988, Pat. No. 4,845,267.

[51] Int. Cl.$^5$ .............................. C25B 3/02
[52] U.S. Cl. ............................ 204/79; 204/78
[58] Field of Search ...................... 204/78, 79

[56] References Cited

U.S. PATENT DOCUMENTS

| 3,459,643 | 8/1969 | Ross et al. | 204/59 R |
|---|---|---|---|
| 4,149,941 | 4/1979 | Mitzlaff et al. | 204/78 |
| 4,288,300 | 9/1981 | Mitzlaff et al. | 204/79 |
| 4,326,071 | 4/1982 | Jung | 562/574 |
| 4,528,028 | 7/1985 | Flint et al. | 71/118 |

FOREIGN PATENT DOCUMENTS

53-90220  8/1978  Japan .

OTHER PUBLICATIONS

T. Shono et al., J. Am. Chem. Soc. 97,4264 (1974).
T. Shono et al., J. Org. Chem. 52,536 (1987).
T.Fuchigami et al., J. Org. Chem. 52,5489 (1987).
T. Fuchigami et al., Tetrahedron Letters 27, 3869 (1986).
Eberson and Utley in *Organic Electrochemistry 2nd Ed*, pp. 779-783, 1983, edited by M. Baiser and H. Lund, 1983.
R. B. Silverman et al., J. Org. Chem. 45,815 (1980).

*Primary Examiner*—John F. Niebling
*Assistant Examiner*—Steven P. Marquis
*Attorney, Agent, or Firm*—D. Wendell Osborne

[57] ABSTRACT

Alkyl esters of 2-fluoro-1-methoxyethylcarbamic acid, which are useful intermediates in the preparation of compounds, such as 4-amino-5-fluoropentanoic acid, are prepared by the electrochemical anodic oxidation of esters of 2-fluoroethylcarbamic acid in the presence of methanol and an electrolyte.

11 Claims, No Drawings

ALKYL 2-FLUORO-1-METHOXYETHYLCARBAMATES

CROSS REFERENCE TO RELATED APPLICATION

This is a divisional, of application Ser. No. 154,762, filed Feb. 11, 1988 now U.S. Pat. No 4,845,267.

BACKGROUND OF THE INVENTION

The present invention relates to alkyl esters of 2-fluoro-1-methoxyethylcarbamic acid, which are useful as chemical intermediates, and to a method of preparation of the esters.

The preparation of many biologically active compounds, including pharmaceutical, herbicidal and fungicidal compounds, is greatly complicated by the absence of appropriate chemical intermediates. As a result, the commercial development of these compounds is often delayed or made impractical. Amino acid derivatives containing beta-fluoroethylamine moieties, such as those described in U.S. Pat. Nos. 4,326,071 and 4,528,028, are one such type of compound. The known methods of preparation of these compounds utilize expensive raw materials, generate copious amounts of waste, and are generally unsuited to large scale manufacturing operations. For example, 4-amino-5-fluoropentanoic acid is reported in the *Journal of Organic Chemistry*, 45, 815 (1980), to be prepared from glutamic acid in a multistep process involving cyclization to a pyrrolidone and subsequent reopening of the ring and concluding with a fluoride exchange using silver fluoride. Better methods of preparation of amino acid derivatives containing betafluoroethylamine moieties which avoid these problems would greatly advance the art.

SUMMARY OF THE INVENTION

It has now been found that alkyl2-fluoro-1-methoxyethylcarbamates can be prepared from alkyl 2-fluoroethylcarbamates by electrochemical anodic oxidation in the presence of methanol and that these compounds are useful in the preparation of 4-amino-5-fluoropentanoic acid and its salts, which are known pharmacological agents and herbicides.

Thus, a compound of Formula I (below)

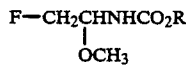

wherein R represents $C_1$–$C_4$ alkyl is prepared by a process comprising passing an electrical current through a mixture containing a $C_1$–$C_4$ alkyl 2-fluoroethylcarbamate, an electrolyte and methanol under conditions conducive to electrochemical oxidation.

The invention encompasses the compounds of Formula I as well as their preparation.

DETAILED DESCRIPTION OF THE INVENTION

The compounds of Formula I are the $C_1$–$C_4$ alkyl esters of 2-fluoro-1-methoxyethylcarbamic acid. This includes the methyl, ethyl, propyl, butyl, 1-methylethyl, 1-methylpropyl, 2-methylpropyl, 1,1-dimethylethyl, and cyclopropylmethyl esters.

The compounds of Formula I can be prepared by the electrochemical anodic oxidation of $C_1$–$C_4$ alkyl esters of 2-fluoroethylcarbamic acid in the presence of methanol under conditions conducive to the transformation.

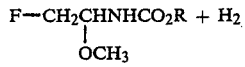

Any electrochemical cell that is compatible with the reagents and reaction conditions can be employed. It is, however, often preferable to employ a flow-through type electrochemical cell and to conduct the process in a continuous manner. Cells equipped with carbon electrodes having a large surface area are preferred. Electrodes of many other compositions are also useful. The cells described in the *Journal of the American Chemical Society*, 97, 4164 (1975), are typical of laboratory batch reactors that are useful.

The process is typically conducted by mixing the ester of 2-fluoroethylcarbamic acid with excess methanol and other reagents to obtain a mixture containing about 3 to about 50 percent of the ester. The molar ratio of methanol to ester employed is generally greater than about 4. A sufficient amount of an electrolyte, such as tetraethylammonium p-toluenesulfonate, is used to make the solution contain about 1 to about 20 percent electrolyte. Tetraalkylammonium salts of strong acids, particularly sulfonic acids, are especially useful electrolytes, but any electrolyte that is soluble in the medium and unreactive under the conditions of the process can be employed. A small amount of a base, generally less than about 10 mole percent of the ester present, is optionally used to insure that the medium does not become excessively acidic. Any base that does not interfere with the electrochemical oxidation process can be employed, but alkali metal carbonates, such as sodium carbonate, are preferred. Other reagents that do not react in the system or otherwise interfere with the process, such as auxiliary solvents and solubilizing agents, can be present as well. Acetonitrile is a typical auxiliary solvent. Water is generally deleterious to the process and substantially anhydrous conditions are preferred. The reagents can be mixed in any order.

The mixture to be electrolyzed is either prepared in an electrochemical cell or pre-prepared and added to an electrochemical cell to conduct the process. A voltage sufficient to create a current of from about 0.1 to about 25 amperes is applied to the electrodes and the temperature is generally maintained below about 50° C. Currents of between about 0.5 and 18 amperes and temperatures between about 0° and about 40° C. are preferred. The mixture is generally agitated within the cell by stirring or by allowing the mixture to flow through the cell. The electrolysis is continued until a majority of the ester reactant has been consumed. The exact time required will depend on the conditions employed, primarily on the current, but generally ranges from about 4 hours to about 10 days. It is preferable to carry out the process under conditions whereby less than 2 days is required.

The product of Formula I can be recovered from the mixture obtained in the process by conventional means. Generally, the volatile components of the mixture are removed by evaporation under reduced pressure and the residue is dissolved in a water-immiscible solvent, such as ether or methylene chloride. The resulting solution is extracted with saturated aqueous sodium bicarbonate and saturated aqueous sodium chloride, is dried over magnesium sulfate. The solvent is then removed by evaporation under reduced pressure to obtain the product as an oil. The product can be further purified by conventional means, such as by preparative liquid chromatography or by distillation under reduced pressure.

The $C_1$-$C_4$ alkyl esters of 2-fluoroethylcarbamic acid employed as starting materials in the process of the present invention are generally known in the art. They can be prepared from fluoroacetamide, a readily available compound, by reduction with boron hydride and subsequent acylation with an appropriate alkyl chloroformate using procedures described in the *Journal of Organic Chemistry*, 29, 2870 (1964) and the *Journal of the Chemical Society*, 1950, 1067.

The preparation of 4-amino-5-fluoropentanoic acid from the compounds of Formula I can be accomplished by the steps of condensation with allyltrimethylsilane in the presence of titanium tetrachloride to obtain an alkyl 1-(fluoromethyl)-3-butenylcarbamate intermediate, hydroboration with dicyclohexylboron hydride and hydrolysis with sodium hydroxide and hydrogen peroxide to obtain an alkyl 1-(fluoromethyl)-4-hydroxybutylcarbamate as an intermediate, and oxidation with potassium permanganate and hydrolysis with hydrochloric acid as illustrated below.

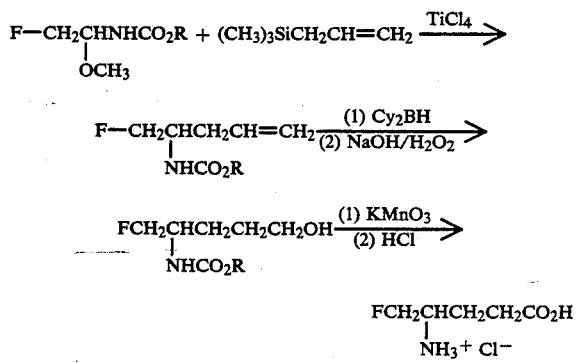

Alternate reagents for each of the reagents involved in the transformation described above will be readily apparent to those skilled in the art.

The following examples are presented to illustrate the invention and should not be construed as limitations to its scope.

EXAMPLE 1

Preparation of Methyl 2-Fluoro-1-methoxyethylcarbamate by Electrochemical Oxidation A 100 ml beaker was fitted with two 0.5 cm diameter carbon electrodes, a silver/silver nitrate reference electrode, a Teflon ® stirring bar, a thermometer, and an external water-cooled bath containing ethylene glycol. A mixture of 15.7 g (0.13 mol) of methyl 2-fluoroethylcarbamate, 6 g (0.02 mol) of tetraethylammonium p-toluenesulfonate, and 60 ml of methanol was prepared in the beaker and then a constant current of 0.40–0.45 ampere was passed through the cell for 7 days while stirring and maintaining the temperature at about 25° C. with the bath. The solvent and other volatiles were removed by evaporation under reduced pressure and the residue was dissolved in 100 ml of ether. The resulting solution was extracted with 10 ml of water, 25 ml of water saturated with sodium bicarbonate, and 25 ml of water saturated with sodium chloride and was then dried over magnesium sulfate. The volatiles were then removed by evaporation under reduced pressure to obtain 17.5 g of a light yellow oil which was about 67 percent the desired product. This was purified by liquid chromatography, eluting with 20:80 acetone-hexane, to obtain 12.7 g (about 50 percent of theory) of the title compound in about 77 percent purity. This was fractionally distilled to obtain 6.6 g of the desired product, which boiled at 55°–56° C. at 0.05 mm Hg pressure and had the following absorptions in its proton nmr spectrum in deuterochloroform: δ 3.43 (s, 3H), δ 3.74 (s, 3H), δ 4.37 (dd, 2H, J=4.1, 46.6 Hz), δ 5.08 (m, 1H).

Elemental analysis: Calculated for $C_5H_{10}FNO_3$: C, 39.73; H, 6.67; N, 9.27; Found: C, 39.83; H, 6.76; N, 9.02.

EXAMPLE 2

Preparation of Methyl 2-Fluoro-1-methoxyethylcarbamate by Electrochemical Oxidation in a Flow-cell An undivided electrochemical flow cell was constructed from two 150 cm² graphite block electrodes separated with a 6 mm Viton ® gasket and plumbed to a 500 ml jar reservoir, a Teflon ® lined pump and a refrigerated cooling system so that the contents of the reservoir could be continuously recirculated thorugh the cell and cooling system. The electrodes were connected to a power source and a voltage meter. The system was flushed with chromatography grade methanol to remove any contaminants. The reservoir was charged with 10–20 g of molecular sieves to keep the system dry, 290 g of chromatography grade methanol, 12 g (0.039 mol) of tetraethylammonium p-toluenesulfonate, 2 g (0.02 mol) of sodium carbonate, and 27.5 g of 91 percent purity (0.227 mol) of methyl 2-fluoroethylcarbamate and the resulting solution was circulated through the electrochemical cell while maintaining the current at 10 amperes and the temperature at 12°–16° C. After 1 hour gas chromatographic analysis indicated about 2 percent conversion. The current was increased to 12 amperes and the conversion went up to about 8 percent during the next hour and 39 percent after 6 hours. The process was continued overnight to increase the conversion to about 95 percent based on starting material and 81 percent based on product. The volatiles were removed under reduced pressure and the residue was dissolved in 200 ml of methylene chloride. The resulting solution was extracted with 100 ml of water, 100 ml of saturated aqueous sodium bicarbonate, and 100 ml of saturated aqueous sodium chloride and dried over magnesium sulfate. Evaporation of the volatiles under reduced pressure left 22.0 g of an oily residue which was found to be the title compound of about 81 percent purity by gas chromatography. The aqueous extracts were combined and extracted with methylene chloride to obtain another 7.6 g of the title compound of about 85 percent purity. The total yield recovered was about 85 percent of theory.

EXAMPLE 3

Preparation of Methyl 1-(Fluoromethyl)-3-butenylcarbamate

A solution of 8.0 g of methyl 2-fluoro-1-methoxyethylcarbamate of about 85 percent purity (0.053 mol)

and 9.26 ml (0.058 mol) of allyltrimethylsilane in 50 ml of methylene chloride was prepared, blanketed with nitrogen, and cooled to −75° C. A 1M solution of titanium tetrachloride in methylene chloride (57 ml, 0.057 mol) was added over a 15 min period and the mixture was allowed to stir at −75° C. for 1 hour. It was then allowed to warm to 0° C. and stir over 1 hour before being poured into a mixture of 100 ml of methylene chloride and 100 ml of cold saturated aqueous sodium chloride. The layers were separated and the organic layer dried over magnesium sulfate and filtered through celite. The volatiles were removed by evaporation under reduced pressure and the residue distilled to obtain 7.2 g of the title compound, which distilled at 68°–69° C. at 0.25 mm Hg pressure and had the following absorptions in its proton nmr spectrum in deuterochloroform: $\delta$ 2.37 (t, 2H, J=7 Hz), $\delta$ 3.65 (s, 3H), $\delta$ 4.43 (dd, 2H, J=4.0, 45 Hz), $\delta$ 4.9 (m, 1H), $\delta$ 5.75 (m, 1H).

Elemental Analysis: Calculated for $C_7H_{12}FNO_2$: C, 52.16; H, 7.51; N, 8.69; Found: C, 51.59; H, 7.22; N, 8.48.

EXAMPLE 4

Preparation of Methyl 1-(Fluoromethyl)-4-hydroxybutylcarbamate

Seven ml of tetrahydrofuran were placed in a dried, argon-flushed 50 ml flask equipped with a septum, an argon inlet, and a spin bar and 7.0 ml of a 1M solution of borane in tetrahydrofuran was added. Cyclohexene (1.4 ml, 13.8 mmol) was added with stirring and cooling with an ice bath. The bath was removed and the mixture allowed to warm and stir overnight during which time a white precipitate formed. A solution of 1.00 g of methyl 1-(fluoromethyl)-3-butenylcarbamate (6.20 mmol) dissolved in 2.0 ml of ether was added rapidly to the mixture with stirring. The mixture exothermed slightly and the white precipitate dissolved. After 4 hours the solution was cooled with an ice bath and 3.0 ml of 4.0N sodium hydroxide added. There was some gas evolution. Four ml of 30 percent hydrogen peroxide was added dropwise with stirring over several minutes and the mixture was allowed to warm and stir for 20 min at which time it was transferred to a separatory funnel containing 80 ml of ethyl acetate and 20 ml of water. The aqueous layer was removed and the organic layer extracted with 20 ml of aqueous sodium chloride solution. The combined aqueous layers were extracted with ethyl acetate and the organic layers were then combined, dried over magnesium sulfate, and filtered. The volatiles were then removed by evaporation under reduced pressure to obtain the title compound as a clear, viscous oil. This was purified by bulb-to-bulb distillation to obtain 0.89 g of the desired product (80 percent of theory) containing less than 2 percent of isomers and having carbon, fluorine, and proton nmr spectra consistent with the assigned structure.

Elemental Analysis: Calculated for $C_7H_{14}FNO_3$: C, 46.92; H, 7.87; N, 7.82; Found: C, 46.84; H, 7.61; N, 7.74.

EXAMPLE 5

Preparation of 4-Carboxymethylamino-5-fluoro-pentanoic Acid

One gram (5.58 mmol) of methyl 1-(fluoromethyl)-4-hydroxybutylcarbamate was dissolved in 40 ml of benzene in a 100 ml flask and 0.20 g of dicyclohexyl-18-crown-6ether and 0.90 g (5.7 mmol) of powdered potassium permanganate were added with stirring to obtain a deep purple solution containing suspended dark solids. After 1.5 hour an additional 1.0 g (6.3 mmol) of potassium permanganate was added and the suspension allowed to stir overnight at room temperature. The solids were collected by filtration, extracted with benzene to remove the crown ether complex, and then extracted three times with 10 percent potassium hydroxide solution. The purple potassium hydroxide extracts were combined and treated with sodium bisulfite, filtered, and acidified with concentrated hydrochloric acid to obtain a clear solution. This was thrice extracted with 100 ml portions of ethyl acetate and the combined organic extracts were dried over magnesium sulfate. The volatiles were removed by evaporation under reduced pressure to obtain 0.70 g (65 percent of theory) of the title compound as a clear, viscous oil. The proton and carbon nmr spectra and ir spectrum of this oil were consistent with the assigned structure.

Elemental Analysis: Calculated for $C_7H_{11}FNO_4$: C, 43.52; H, 6.26; N, 7.25; Found: C, 43.46; H, 6.06; N, 6.51.

EXAMPLE 6

Preparation of 4-Amino-5-fluoropentanoic Acid

A mixture of 0.65 g (3.4 mmol) of 4-carboxymethylamino-5-fluoropentanoic acid and 10 ml of concentrated hydrochloric acid was prepared in a 50 ml flask and heated at reflux overnight. The volatiles were then removed by evaporation under reduced pressure and the gummy residue was dissolved in water and purified by ion exchange chromatography using DOWEX® 50 X-8 resin. The solution was loaded onto the rinsed column, washed with water, and eluted with 6 percent aqueous hydrochloric acid. Evaporation of the product-containing fractions gave 0.42 g (71 percent of theory) of the title compound as an oily crystalline material which tenaciously retained water. This was recrystallized from ethyl acetate/acetic acid to obtain the desired product as white crystals melting at 129° –134° C. and having the expected proton and carbon nmr spectra.

What is claimed is:

1. A process for the preparation of a compound of the formula

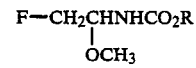

wherein R represents $C_1$–$C_4$ alkyl
which comprises passing an electrical current through a mixture containing a $C_1$–$C_4$ alkyl 2-fluoroethylcarbamate, an electrolyte and methanol under conditions conducive to electrochemical oxidation.

2. A process according to claim 1 wherein the mixture also contains a non-interfering base.

3. A process according to claim 2 wherein the base is an alkali metal carbonate.

4. A process according to claim 3 wherein the alkali metal carbonate is sodium carbonate.

5. A process according to claim 1 wherein the compound prepared is additionally recovered.

6. A process according to claim 1 wherein the electrolyte is a tetraalkylammonium salt of a sulfonic acid.

7. A process according to claim 1 wherein R represents methyl.

8. A process according to claim 7 wherein the mixture also contains a non-interfering base and the electrolyte is a tetraalkylammonium salt of a sulfonic acid.

9. A process according to claim 1 wherein a current of about 0.5 to about 18 amperes is passed through the mixture.

10. A process according to claim 1 wherein the temperature is maintained between about 20° and about 40° C.

11. A process according to claim 1 wherein the mixture is substantially anhydrous.

* * * * *

UNITED STATES PATENT AND TRADEMARK OFFICE
CERTIFICATE OF CORRECTION

PATENT NO. : 4,927,508

DATED : May 22, 1990

INVENTOR(S) : James M. Renga, Charles K. Bon, Aylin H. Gulbenkian, Michael G. Smith It is certified that error appears in the above-identified patent and that said Letters Patent is hereby corrected as shown below:

On the cover sheet, under "Inventors:", "Charles K. Bon" has been misspelled;

Col. 1, line 39, between "alkyl" and "2" insert a space;

Col. 3, lines 36-40, change the third formula as follows:

;

Col. 4, line 29, "through" has been misspelled;

Col. 5, line 66, between "6" and "ether" insert a space;

Col. 8, line 1, delete "20°" and insert -- 0°C --.

Signed and Sealed this

Seventh Day of April, 1992

Attest:

HARRY F. MANBECK, JR.

*Attesting Officer*      Commissioner of Patents and Trademarks